United States Patent [19]

Golstein et al.

[11] 4,440,903
[45] Apr. 3, 1984

[54] DIHALOISOCYANIDE DERIVATIVES OF POLYMERS FOR COUPLING NUCLEOPHILES

[75] Inventors: Leon Golstein, Rehovot; Mordechai Sokolovsky, Tel-Aviv; Amihay Freeman, Rishon Lezion, all of Israel

[73] Assignee: Ramot University Authority for Applied Research and Industrial Development Ltd., Tel-Aviv, Israel

[21] Appl. No.: 921,055

[22] Filed: Jun. 30, 1978

[51] Int. Cl.³ .................. C12N 11/08; C12N 11/06; C07G 7/00; C07C 143/00

[52] U.S. Cl. .................. 525/54.1; 260/543.2; 435/180; 435/181; 525/921; 528/259; 528/332; 564/148

[58] Field of Search ............ 195/63, 68, DIG. 11; 260/8, 23 TM, 23.7 H, 112 R, 6, 29.4 UA; 424/94; 252/441; 528/291, 362; 435/174, 180, 181, 176

[56] References Cited

U.S. PATENT DOCUMENTS

| | | | |
|---|---|---|---|
| 3,619,371 | 11/1971 | Crook et al. | 435/181 X |
| 3,933,589 | 1/1976 | Keyes | 195/68 |
| 3,970,597 | 7/1976 | Sokolovsky et al. | 435/180 X |
| 4,034,139 | 7/1977 | Mazarguil et al. | 195/68 X |
| 4,071,409 | 1/1978 | Messing et al. | 435/176 |
| 4,098,645 | 7/1978 | Hartdegen et al. | 195/68 |
| 4,115,305 | 9/1978 | Hornby et al. | 195/63 X |
| 4,115,305 | 9/1978 | Hornby et al. | 435/181 X |

OTHER PUBLICATIONS

Kuehle et al., "New Methods . . . ; Syntheses of Isocyanide Dihalides", Angew. Chem. Internat. Edit., vol. 6, #8, 1967, pp. 649–665.
Kuehle, E., "New Methods . . . ; Reactions of Isocyanide Dihalides and their Derivatives", Angew. Chem. Internat. Edit., vol. 8, #1, 1969, pp. 20–34.
Sundaram et al., Preparation and Properties of Vlease Chemically Attached to Nylon Tube, FEBS Letters, vol. 10, No. 5, 1970, (pp. 325–327).
Goldstein et al., Chemically Modified Nylons as Supports for Enzyme Immobilization, Biochem. J., vol. 143, 1974, (pp. 497–509).
Zabarsky, O., Immobilized Enzymes CRC Press, Cleveland, Ohio, 1973, (pp. 10–20).
Axen et al., The Use of Isocyanides for the Attachment of Biologically Active Substances to Polymers, ACTA Chemice Scandinavica, vol. 25, 1971, (pp. 1129–1169).
Singer, S. J., Preparation of an Electron-Device Antibody Conjugate, Nature, vol. 183, 1959, (pp. 1523–1524).
Day et al., Organic Chemistry. D van Nostrand Co., Inc., N.Y., 1960, (pp. 742, 746 & 747).
Goldstein et al., Chemically Modified Polymers Containing Isocyanide Functional Groups as Supports for Enzyme Immobilization, Biotechnological Applications of Proteins and Enzymes, Academic Press, N.Y., 1977, (pp. 153–167).
Ulrich et al., Syntheses and Reactions of Isocyanide Dihalides, The Chemistry of Cyanates and their Thio Derivatives, part 2, John Wiley & Sons, N.Y., 1977, (pp. 969–1001).

Primary Examiner—David M. Naff
Attorney, Agent, or Firm—Browdy and Neimark

[57] ABSTRACT

The present invention relates to novel key intermediates for the production of biologically active compounds coupled to polymers, of the general formula P—$NCX_2$, wherein X designates a halogen atom selected from chlorine and bromine, and wherein P designates the polymer backbone of a polymer of the polyamide, polyester and ureaformaldehyde type. The invention further relates to compounds obtained by the reaction of the above compound P—$NCX_2$ with a bifunctional or polyfunctional nucleophile. Suitable nucleophiles are hydrazides of dicarboxylic acids and amongst these there may be mentioned polyacrylamides partially substituted with acylhydrazide groups; polyfunctional amines selected from alkylamines, aralkylamines, arylamines and macromolecular compounds containing amino groups. The key intermediate $PNCX_2$ may be coupled directly to biologically active macromolecules and amongst the preferred compounds of this type there are the various biologically active proteins and enzymes. The coupling of the biologically active macromolecules may also be effected via hydrophilic polymer moieties first grafted onto the polymer P via said dihaloisocyanide groups.

4 Claims, No Drawings

DIHALOISOCYANIDE DERIVATIVES OF POLYMERS FOR COUPLING NUCLEOPHILES

FIELD OF THE INVENTION

The present invention relates to novel dihaloisocyanide derivatives of polymers and to products obtained by coupling to these key intermediates various nucleophiles. The preferred new compounds are dihaloisocyanide derivative of polymers selected from various types of polyamides, polyesters and urea-formaldehyde polymers wherein halo designates chlorine or bromine. When such dihaloisocyanide polymers are coupled with nucleophiles there are obtained various valuable products. The dihaloisocyanides can be coupled with biologically active macromolecules such as proteins, and the biological activity of these is retained to a large degree. The dihaloisocyanide polymers can be first reacted with a polymer containing nucleophilic groups capable of undergoing reaction with the dihaloisocyanide groups and the resulting product can be used for coupling biologically active macromolecules. Amongst preferred polymers coupled to the dihaloisocyanide polymers there may be mentioned hydrophilic polymers, and when the product is coupled with biologically active macromolecules the stability of the biologically active product is enhanced. The invention further relates to a process for the production of the various above defined novel products and more specifically to the production of the dihaloisocyanide substituted polymers and to the production of the various products obtainable therefrom by reaction with suitable nucleophiles.

BACKGROUND OF THE INVENTION

There is known a method for the direct covalent bonding of biologically active molecules to chemically modified polyamides, such as various types of nylon (nylon 6, nylon 66). The known method involves a 4-component condensation reaction of an amine, a carboxyl moiety, an aldehyde, and an isocyanide: generally the polymeric carrier provides the isocyanide moieties, and the protein the amine or the carboxyl moieties, an aldehyde and the forth component being added to the reaction mixture. It is one of the drawbacks of this known method that the biological activity of certain compounds is impaired by the aldehyde.

SUMMARY OF THE INVENTION

According to the present invention, there is provided a novel type of modified polymeric carriers which are very reactive and which are utilized for the covalent bonding of biologically active proteins. The novel polymeric carriers are strongly electrophilic dihaloisocyanide derivatives. The preferred dihaloisocyanides are dibromoisocyanides, the second choice being dichloroisocyanide derivatives. The invention is illustrated mainly with reference to the dibromo derivatives, but the corresponding dichloro derivatives can also be used.

In the most general terms P designates a suitable polymeric backbone, and the starting material is thus a derivative thereof with $-N\!=\!C$ functional groups, which is converted to

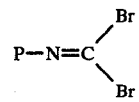

derivatives or to

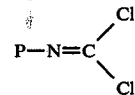

derivatives which can be reacted with various compounds having at least one nucleophilic group, resulting in the coupling of such compounds to the polymeric backbone. Amongst nucleophiles which can be used there may be mentioned various bifunctional or polyfunctional amines, such as alkylamines, arylamines, aralkylamines and macromolecular compounds containing amine groups. The polymer can be modified by reacting it with another polymer containing suitable nucleophilic groups. Amongst suitable nucleophiles there are polyacrylamides partially substituted with acylhydrazide groups, hydrazides of dicarboxylic acids, polyamines such as linear polyvinylamine, and various biologically active macromolecules having suitable functional groups for reaction with the dihaloisocyanide polymer. Amongst these there may be mentioned enzymes. Various suitable polymeric backbones may be used. Especially suitable are the various types of commercially available polyamides of the various nylon types (such as Nylon 6, Nylon 66, AA and AB-BB types), various polyesters and polymers of the urea-formaldehyde type. The novel dihaloisocyanide polymers can be used for the covalent bonding of biologically active proteins:

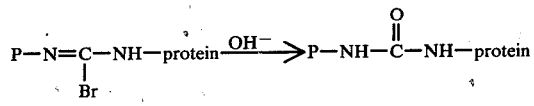

wherein the $-NH_2$ group is part of the protein molecule.

The highly reactive insoluble polymeric dihaloisocyanide derivative is to a certain extent a polymeric structural analog of phosgene and this easily reacts with unprotonated forms of the nucleophilic groups present in proteins, and when the amine function of the protein undergoes reaction, a stable ureide type of bond is formed. With aromatic hydroxyls and with sulfhydryl groups there are obtained corresponding urethane and thiolurethan derivatives, respectively.

The haloisocyanide substituted polymer is highly reactive and when such polymer is powder form is added portionwise to a cold aqueous solution of a biologically active protein, as for example an enzyme, the reaction proceeds to completion in about 30 minutes in the cold.

The dihaloisocyanide polymers can be used as starting material for the prouction of various other products, by reaction with multifunctional reagents containing at least one nucleophilic group capable of reacting with the dihaloisocyanide moiety. For example, reaction with acylhydrazides to form 5-membered 1,3,4-oxadiazole type heterocyclic compounds can be utilized to prepare polymeric acylhydrazide derivatives: Dibromoisocyanide nylon was reacted with bifunctional adipic dihydrazide, which later can be converted to the corresponding azide by treatment with nitrous acid, and used for the covalent bonding of proteins.

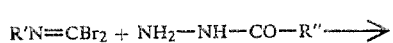
(II)

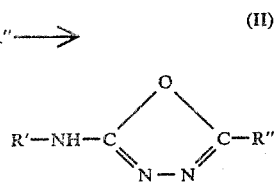

wherein
R' is a polymeric backbone and
R" is the residue of a acyl hydrazide.

In a similar manner polymeric hydrazides can be grafted onto the surface of dibromo- or dichloro-substituted isocyanide polymers. For example, linear polyacrylamide in which a certain percentage (of about 5 to 10%) of the amide groups had been converted to acylhydrazide groups by controlled hydrazinolysis according to Inman (Inman J. K. and Dintizis H. M. Biochemistry 8, 4074 (1969), Inman J. K. Meth. Enzymol. 34, 40 (1974)), was reacted with dibromoisocyanide nylon to yield a novel polymeric carrier bearing acylhydrazide groups. The acylhydrazide groups can be used for the immobilization of enzymes by the azido method; the acylhydrazide groups can also be converted into other chemically active functional groups and the latter can be used for the immobilization of biologically active proteins. Conversion of the acylhydrazide to an arylamine followed by a diazotization can be used for the coupling of proteins via azo-bonds.

It is one of the main advantages of the present invention that:
a. the protein binding capacity, and
b. the specific activity
of the covalently bound protein is considerably higher with the polymer polyacrylamide grafts as compared with the ungrafted polymer. Furthermore, enzymes and other active molecules, bound to polyacrylamide graft-polymers exhibited enhanced storage and thermal stability.

The polymeric dihaloisocyanide derivatives can be used for grafting of other polymers containing other types of nucleophilic functional groups, such as for example by reacting bromoisocyanide nylon with linear polyvinylamine to give polyvinylamine nylon grafts.

The invention is illustrated in the following with reference to preparations wherein fine powders of isocyanide and dihaloisocyanide-substituted polymers obtained from polyamides, polyesters and urea-formaldehyde resins are used because of the favorable area to weight ratio of such material as support. Other polymers with =N'=C groups can be used in a similar manner. The polymers can be used in any desired form such as fibers, sheets, non-woven fabric etc.

DESCRIPTION OF THE PREFERRED EMBODIMENT

METHOD 1,6-diisocyanohexane was synthesized according to Goldstein et al (Biochem J. 143, 497 (1974)). The isocyanide content of polymers containing isonitrile functional groups was determined tritrimetrically by an adaptation of the method of Aurora et al (Z. Anal.-Chem. 269, 124 (1974)).

Dibromoisocyanide groups were estimated by reacting the $NCBr_2$ polymers with excess dithioerythritol, the unreacted sulfhydryl groups being determined spectrophotometrically by the Ellman procedure (Arch. Biochem. Biophys. 82, 70 (1959)).

Acylhydrazide groups were determined by a two-step procedure, consisting of succinylation followed by the titrimetric determination of carboxyls, essentially as described by Inman (Meth. Enzymol. 34, 30 (1974)).

Bound protein was estimated by the Lowry method and confirmed by total amino acid analysis of acid hydrolyzates of the appropriate enzyme-polymer conjugate. The enzymatic activities of the trypsin, chymotrypsin, subtilisin BPN', and papain and of their insoluble conjugates were determined at 25° by the pH-stat-method (Golstein, Meth. Enzymol. 19, 915 (1970)).

The enzymic activity of urease and immobilized urease was determined by the nitropruside method according to Chaney and Marbach (Clin.Chem. 8, 130 (1962)).

EXAMPLE 1

ISOCYANIDE DERIVATIVES OF NYLON-(Polyisonitrile-nylon)

The isocyanide-derivative of nylon was prepared from partially hydrolyzed nylon powder essentially as described by Golstein et al (Biochem. J. 143, 497 (1974)). Nylon powder (2 gms) was suspended in 3 N HCl (60 ml), stirred for 4 hrs at room temperature, and then washed with water, methanol, and ether and air-dried. The partially hydrolyzed nylon powder (1 mg, 60–70 μmole COOH/gm) was suspended in propan-2-ol (40 ml). Isobutyral (16 ml) was then added, followed by 1,6-diisocyanohexane (4 ml; 0.03 mole) and the reaction allowed to proceed with stirring, in a closed vessel at room temperature, for 24 hrs. The polyisonitrile-nylon powder was separated by filtration, washed with methanol and ether and air-dried. The mean isocyanide content of the powder was 40–50 equiv×$10^{-6}$/gm (See Table I).

EXAMPLE 2

ISOCYANIDE DERIVATIVES OF SYNTHETIC POLYESTERS

Isocyanide functional groups were introduced on the surface of poly(ethyleneterephthalate) powders of fibers by a three-step procedure, based on the Passerini reaction

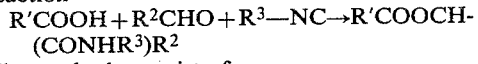

The methods consist of:
a. controlled alkaline hydrolysis to generate —COOH.HO— pairs on the surface of the polyester structure,
b. conversion of the hydroxyl groups generated in the first step into aldehydes by controlled oxidation with dipyridyl chromium (VI)oxide according to Stensio (Acta Chem. Scand. (1971) 25, 1125–1128), and
c. resealing of the carboxyl-aldehyde pairs by a Passerini type reaction using 1,6-diisocyanohexane.

Procedure:
a. Poly(ethyleneterephthalate) powder (1 gm) was suspended in 0.01 N NaOH in 10% ethanol (50 ml)

and stirred for 1 hr at 33°. The powder was separated by filtration, washed with water, 0.01 N HCl, water, methanol, ether, and air-dried.

b. The partially hydrolyzed polyester powder (1 ml) was suspended in glacial acetic acid (10 ml). An 0.8 M solution of dipyridyl chromium (VI) oxide was added and the reaction mixture stirred for 2 hrs. at room temperature. The powder was washed exhaustively with water, methanol, and ether and air-dried.

c. The oxidized poly(ethyleneterephthalate) powder obtained in the preceding step was suspended in ether (10 ml), 1,6-diisocyanohexane (1 ml) was added and the reaction allowed to proceed at room temperature for 18 hrs. The powder was separated, washed with ether, methanol and again with ether and air-dried. The mean isocyanide content of the powder was 40–50 equiv$\times 10^{-6}$/gm. (See Table I).

EXAMPLE 3
ISOCYANIDE DERIVATIVES OF UREA-FORMALDEHYDE RESINS

Isocyanide functional groups were introduced on the surface of urea-formaldehyde resin powders using a two-step procedure:

a. mild acid hydrolysis to generate amino groups through degradation of ureide sequences on the surface of the polymer, b. four-component condensation in the presence of acetic acid, isobutyral and 1,6-diisocyanohexane in methanol.

Procedure:

a. Urea-formaldehyde resin powder (1 gm) was suspended in 3 N HCl (20 ml) and stirred at room temperature for 45 min. The powder was separated and washed with water 0.1 N NaOH, methanol, and ether and air-dried.

b. Partially hydrolyzed urea-formaldehyde resin powder (1 gm) was suspended in methanol (5 ml). Glacial acetic acid (0.5 ml), isobutyral (0.5 ml) and 1,6-diisocyanohexane (1 ml) were added and the reaction allowed to proceed with stirring at room temperature for 18 hrs. The powder was separated, washed with methanol and ether and air-dried. The mean isocyanide content of the powder was 5–6 equiv$\times 10^{-6}$/gm (See Table VIII).

The properties and protein binding capacities of the isocyanide polymers described in Examples 1 to 3 are summarized in Table I.

EXAMPLE 4
DIBROMOISOCYANIDE NYLON DERIVATIVES

Polyisonitrile-nylon powder (100 mg; 40–50 μmole —NC/gm) was suspended in chloroform (10 ml) and stirred magnetically for 10 min. over ice. A bromine solution (1 ml of a 1% solution in CHCl$_3$; 200 μmole Br$_2$) was added to the ice-cooled polymer suspension and stirred for 15 min. Triethylamine (0.2 ml) was then added with stirring (to remove unreacted bromine). The polymeric powder was separated on a suction filter, washed with cold chloroform and then with ether and air-dried. Due to its high reactivity, the dibromoisocyanide-nylon derivative (30–35 equiv$\times 10^{-6}$—NCBr$_2$/gm) was used immediately after preparation. (See Table II).

EXAMPLE 5
ACYLHYDRAZIDE-NYLON DERIVATIVES

Freshly prepared dibromoisocyanide nylon powder (100 mg; 30–35 μmole —NCBr$_2$/gm) was added slowly to 10 ml of a vigorously stirred, ice-cooled, 0.02 M solution of adipic dihydrazide, brought to pH 8, and the reaction allowed to proceed under the pH-stat for 1 hr. The acylhydrazide-nylon powder was separated on a filter-washed with water, methanol, and ether and air-dried. The polymer (25–30 equiv.$\times 10^{-6}$—CONH.NH$_2$/gm) was stored in stoppered vials at room temperture. (See Table II).

EXAMPLE 6
POLYACRYLAMIDE-NYLON ACYLHYDRAZIDE DERIVATIVES

Freshly prepared dibromoisocyanide nylon powder (100 mg; 30–35 equiv.$\times 10^{-6}$—NCBr$_2$/gm) was added slowly to 10 ml of a vigorously stirred, ice-cooled solution of polyacrylamide-hydrazide (5 mg/ml; acylhydrazide content 5%) in 0.1 M ethylmorpholine buffer pH 8. The reaction was allowed to proceed for 1 hr with stirring. The polyacrylamide-nylon powder was separated by filtration and washed with water, ethanol, ether and air-dried.

EXAMPLE 7
POLYVINYLAMINE-NYLON ISOCYANIDE DERIVATIVE a. Freshly prepared dibromoisocyanide nylon powder (100 mg; 30–35 equiv.$\times 10^{-6}$—NCBr$_2$/gm) was added slowly to 5 ml of a vigorously stirred, ice-cooled solution of polyvinylamine (30 mg/ml) in 0.2 M N-ethylmorpholine buffer pH 9. The reaction was allowed to proceed with stirring for another 30 min. The polyvinylamine-nylon powder was separated on a filter and washed with water, methanol, and ether and air-dried.

b. Polyvinylamine-nylon (100 mg) was suspended in methanol (5 ml). An 0.1% (v/v) solution of isobutyral in methanol (0.2 ml) was added and the suspension stirred for 30 min. at room temperature. 1,6-diisocyanohexane (0.25 ml) and glacial acetic acid (0.15 ml) were then added and the reaction allowed to proceed for 18 hrs. at room temperature. The powder was separated on a filter, washed with methanol, and ether and air-dried. The isocyanide content of the powder was 15–20 equiv.$\times 10^{-6}$/gm. The properties and protein binding capacity of the isocyanide derivatives of polyvinylamine nylon are given in Table I.

EXAMPLE 8
CHEMICAL MODIFICATION OF SPUN-BONDED NYLON FABRIC SHEETS

Discs of 30 mm diameter were cut from spun-bonded nylon fabric sheets (Cerex ®, Monsanto Company) and packed in a glass column (height-50 mm; internal diameter 30 mm) fitted with a fritted glass disc at the bottom and a ground-glass adapter at the top. Constant packing of the discs was maintained by means of an additional fritted-glass disc, held in place by teflon rings of the appropriate thickness. By this arrangement all chemical modification reactions as well as the coupling of enzymes could be carried out consecutively, by circulating the appropriate reagents through the column.

a. Isocyanide-nylon derivatives: 3 N HCl (100 ml) was perfused through a column containing 100 discs (about 6 gms net, Cerex ®) to remove impurities, and 3 N HCl was circulated for 4 hrs at room temperature at a rate of 12–15 ml/min. The column was washed by perfusing water (300 ml) methanol (100 ml) and ether (100 ml). A solution of 1,6-diisocyanohexane (3.3 μl) and isobutyral (13.2 ml) in isopropanol (33 ml) was then circulated at a rate of 0.5–1 ml/min at room temperature, overnight. The column was washed with methanol (100 ml) and ether (200 ml).

b. Dibromoisocyanide-nylon: An ice-cooled 0.1% solution of bromine in chloroform (100 ml) was perfused through a column packed with isocyanide-nylon discs, in the course of 30 min. To remove unreacted bromine, the column was washed with the following ice-cold solutions: chloroform (30 ml), 2% triethylamine in chloroform (25 ml), chloroform (30 ml) and ether (50 ml). Due to the high reactivity of the —NCBr$_2$ groups, the dibromoisocyanide-nylon discs were used immediately for the next step.

EXAMPLE 9
ACYLHYDRAZIDE DERIVATIVES OF NYLON FABRIC DISCS

An ice-cooled 0.05 M solution of adipic dihydrazide in 0.01 M N-ethylmorpholine buffer, pH 8 (50 ml) was perfused through a column packed with dibromoisocyanide-nylon discs; the effluent was collected, the pH brought back to 8, and the reagent solution recirculated through the column for 1 hr at a rate of 5–10 ml/min with cooling. The column was washed with water (300 ml), methanol (100 ml) and ether (50 ml).

EXAMPLE 10
AMINOARYL DERIVATIVES OF NYLON FABRIC DISCS

Aminoaryl derivatives of nylon fabric discs were prepared from isocyanide-nylon utilizing the four-component reaction previously described (1,3). Through a column packed with isocyanide-nylon discs a methanolic solution (40 ml) containing 4,4'-diaminodiphenylmethane (400 mg; 2 mmole), isobutyral (0.1 ml; 1 mmole) and acetic acid (0.2 ml; 3.5 mmole) was circulated at room temperature, for 18 hrs at a rate of 0.5–1 ml/min. The column was washed with dimethylformamide (100 ml), methanol (200 ml) and ether (100 ml).

EXAMPLE 11
ACYLHYDRAZIDE DERIVATIVES OF POLYACRYLAMIDE-NYLON DISCS

An ice-cooled solution of polyacrylamide hydrazide (5 mg/ml; acylhydrazide content about 5%) in 0.01 M N-ethylmorpholine buffer, pH 8 (40 ml) was perfused through a column packed with dibromoisocyanide-nylon discs; the effluent was collected, the pH brought back to 8, and the cooled polyacrylamide solution recirculated through the column for 2 hrs at a rate of 12 ml/min. The column was washed with water (300 ml), methanol (50 ml) and ether (50 ml).

EXAMPLE 12
AMINOARYL DERIVATIVES OF POLYACRYLAMIDE-NYLON DISCS

The aminoaryl derivative of polyacrylamide-nylon was prepared from the corresponding acyl-hydrazide derivative via the acylazide method.

An ice-cooled 1% solution of sodium nitrite in 0.1 M HCl (50 ml) was perfused through a column packed with polyacrylamide-nylon acylhydrazide discs at a rate of 2–3 ml/min. The activated column was washed with cold water (100 ml) and reacted immediately with a 4,4-diaminodiphenyl methane solution (50 ml) circulated through the column at 4° for 18 hrs. The reagent solution was prepared by dissolving 0.5 gms. 4,4'-diaminodiphenyl methane in 25 ml dimethylformamide followed by the addition of 25 ml water with stirring, the pH being adjusted to 9.0. The column was washed with dimethylformamide (100 ml) water (200 ml) methanol (100 ml) and ether (50 ml).

EXAMPLE 13
CHEMICAL MODIFICATION OF NYLON-FIBERS

Commercial nylon 6,6 fibers (3 gms overall weight) were packed in a glass tube (6 mm internal diameter, 40 cm length), in parallel to the tube's axis. The fibers were washed by perfusing 300 ml ether, in the course of 2 hrs to remove lubricants. All further manipulations were carried out as described for nylon fabric discs.

EXAMPLE 14
COUPLING OF ENZYMES TO POLYISONITRILE-NYLON POWDER

Polyisonitrile-nylon powder (50 mg) was suspended in 2 ml of a cold enzyme solution (10 mg protein) in 0.1 M sodium phosphate 0.5 M sodium acetate pH 7.5. Cold acetaldehyde (0.1 ml) was then added and the reaction allowed to proceed overnight with stirring at 4°. The insoluble enzyme derivative was separated by filtration, washed with water, 1 M KCl and again with water, resuspended in water (4 ml) and stored at 4°.

The results for several enzymes are summarized in Tables 1 and IV.

EXAMPLE 15
BINDING OF ENZYMES TO DIBROMOISOCYANIDE-NYLON POWDER

Freshly prepared dibromoisocyanide-nylon powder (50 mg) was added in the course of 10 min to a magnetically stirred, ice-cooled solution of enzyme (10 mg) in 2 ml 0.2 M N-ethylmorpholine buffer pH 8.0. The reaction was allowed to proceed for 20 min. The insoluble enzyme derivative was separated by filtration, washed and stored as described above. The results for several enzymes are summarized in Tables III and IV.

EXAMPLE 16
COUPLING OF ENZYMES TO ACYLHYDRAZIDE-NYLON POWDER

Acylhydrazide-nylon powder (50 mg) was suspended in 5 ml cold 0.1 M HCl. Sodium nitrite (50 mg) was then added and the reaction mixture stirred for 30 min. over ice. The acylazide-nylon derivative was separated by filtration, washed exhaustively with cold water and added to a cold solution of the enzyme (10 mg/2 ml) in 0.1 M N-ethylmorpholine buffer pH 9. The reaction was allowed to proceed overnight, with stirring at 4°. The immobilized enzyme derivative was separated by filtration, washed and stored as described above. The results for several enzymes are summarized in Table IV.

EXAMPLE 17
COUPLING OF AMINO ACIDS AND PEPTIDES TO DIBRIOMOISOCYANIDE-NYLON POWDER

Freshly prepared dibromoisocyanide-nylon powder (40 mg) was added in the course of 10 min to a magnetically stirred, ice-cooled, 0.01 M solution of an amino acid derivative or peptide (10 ml), under the pH-stat, set at the appropriate pH. The reaction was allowed to proceed for 20 min, the insoluble derivative was separated by filtration, washed exhaustively with water, methanol and ether and air-dried. The results for several peptides and mixtures thereof are summarized in Table V.

EXAMPLE 18
COUPLING OF ENZYMES TO ACYLHYDRAZIDE DERIVATIVES OF NYLON AND POLYACRYLAMIDE-NYLON DISCS

An ice-cooled 1% solution of sodium nitrite in 0.1 N HCl (100 ml) was perfused through a column packed with nylon- or polyacrylamide-nylon-acylhydrazide discs at a rate of 2-3 ml/min. The activated column was washed with cold water (100 ml). An enzyme solution (5 mg/ml; 40 ml) in 0.1 M N-ethylmorpholine buffer pH 9.0 was then circulated through the column, at 4° for 18 hrs. The column was washed with cold water (500 ml), 1 M KCl (200 ml) and water (100 ml). The enzyme nylon discs were stored under water at 4°. The results for several enzymes are summarized in Tables VIa and VIb. Chymotrypsin and Subtilisin BPN' bound to nylon and polyacrylamide nylon were tested as regards temperature stability. Tests proved that the latter were inactivated at substantially higher temperatures (difference up to about 20° C.).

EXAMPLE 19
COUPLING OF ENZYMES TO AMINOARYL DERIVATIVES OF NYLON AND POLYACRYLAMIDE NYLON DISCS

A column packed with aminoaryl-, nylon or polyacrylamide-nylon discs was activated by circulating 1% sodium nitrite as described above. The activated column was washed with cold water (100 ml). An enzyme solution (5 mg/ml; 40 ml) in 0.1 M phosphate buffer pH 8 was circulated through the column at 4° for 18 hrs. The enzyme-nylon discs were washed and stored as described above. The results for several enzyme are summarized in Tables VIa and VIb.

TABLE I
COUPLING OF TRYPSIN TO ISOCYANIDE DERIVATIVES OF NYLON POLY(ETHYLENETEREPHTHALATE)UREA-FORMALDEHYDE RESIN AND POLYVINYLAMINE-NYLON VIA FOUR COMPONENT CONDENSATION REACTIONS[a]

| Support material | Mean particle Diameter (microns) | Isocyanide content (equiv $\times 10^6$/gm) | Total Bound Protein mg/gm support | Active Bound Protein (% of total) |
|---|---|---|---|---|
| Nylon 6 | 0.7 | 45 | 150 | 56 |
| Poly(ethyleneterephthalate) | 9 | 40 | 93 | 30 |
| Urea-formaldehyde Resin | 200 | 4.8 | 13 | 38 |
| Polyvinylamine nylon | 0.7 | 15 | 50 | 40 |

[a]Coupling mixture: 100 mg polymer and 20 mg trypsin in 4 ml 0,1M phosphate. 0.5M acetate pH 7.5 containing 0.2 ml acetaldehyde

TABLE II
CHARACTERIZATION OF CHEMICALLY MODIFIED NYLONS

| Isocyanide-Nylon Derivative —NC content (equiv $\times 10^6$/gm) | Dibromoisocyanide-Nylon Derivative effective —NCBr$_2$ content (equiv $\times 10^6$/gm) | efficiency of conversion —NC→—NCBr$_2$ (%) | —CONH.NH$_2$content (equiv $\times 10^6$/gm) | Acylhydrazide-Nylon Derivative efficiency of conversion —NCBr$_2$→—CONH.NH$_2$ (%) | overall yield —NC→—CONH.NH$_2$ (%) |
|---|---|---|---|---|---|
| 44 | 31 | 71 | 27 | 87 | 61 |

TABLE III
COUPLING OF ENZYMES TO A DIBROMOISOCYANIDE DERIVATIVE OF NYLON

| Enzyme | pH of coupling reaction | Total bound Protein mg/gm support | Active Bound Protein mg/gm support | Active Bound Protein % of total |
|---|---|---|---|---|
| Trypsin | 7 | 13.1 | 2.0 | 15 |
|  | 8 | 14.2 | 5.5 | 39 |
|  | 9 | 21.0 | 14.2 | 68 |
| Chymotrypsin | 7 | 10.0 | 1.6 | 16 |
|  | 9 | 15.3 | 10.0 | 66 |
| Subtilism BPN' | 7 | 3.3 | 0.14 | 4 |
|  | 9 | 9.3 | 1.14 | 12 |
| Papain | 7 | 26.6 | 3.9 | 15 |
|  | 9 | 23.4 | 11.4 | 49 |

TABLE IV
BINDING OF ENZYMES TO NYLON SUPPORTS CARRYING DIFFERENT FUNCTIONAL GROUPS[a]

| | Isocyanide Derivative[c] | | | Modified Nylon[b] Dibromoisocyanide Derivative[d] | | | Acylhydrazide Derivative[e] | | |
|---|---|---|---|---|---|---|---|---|---|
| | Total bound protein | Active bound protein | | Total bound protein | Active bound protein | | Total bound protein | Active bound protein | |
| Enzyme | (mg/gm support) | mg/gm support | % of total | (mg/gm support) | mg/gm support | % of total | (mg/gm support) | mg/gm support | % of total |
| Trypsin | 48 | 30 | 68 | 21 | 14.2 | 68 | 16.2 | 14.4 | 80 |
| Chymotrypsin | 45 | 10 | 22 | 15.2 | 10 | 66 | 13.6 | 10 | 74 |
| Subtilisin BPN' | 14.4 | 5 | 35 | 9.2 | 1.2 | 13 | 8.6 | 2.8 | 33 |
| Papain | 70 | 32 | 46 | 23.4 | 11.4 | 49 | 29.2 | 12.2 | 42 |

[a] All coupling mixtures contained 10 mg protein and 50 mg derivatized-nylon powder in 2 ml of the appropriate buffer.
[b] Details on chemical characteristics of derivatized-nylon powders are given in Table II.
[c] Coupling of proteins carried out by four component condensation at pH 7.5.
[d] Coupling of protein carried out at pH 9.
[e] Coupling of protein carried out at pH 9.

TABLE V
COUPLING OF MODEL PEPTIDES TO DIBROMOISOCYANIDE-NYLON

| Peptides in Reaction Mixture | pH | Amino Acid Bound (μmoles/gm support) | | | |
|---|---|---|---|---|---|
| | | Leu | His | Tyr | Total |
| Leu NH$_2$ | 7 | 2.2 | — | — | 2.2 |
| | 8 | 9.5 | — | — | 9.5 |
| | 9 | 9.5 | — | — | 9.5 |
| PhCO.Gly.His | 6 | — | 8.4 | — | 8.4 |
| | 7 | — | 11.8 | — | 11.8 |
| | 8 | — | 11.5 | — | 11.5 |
| | 9 | — | 11.3 | — | 11.3 |
| AcTyrOEt | 8 | — | — | 9.1 | 9.1 |
| | 9 | — | — | 12.8 | 12.8 |
| Leu NH$_2$ + PhCO.Gly.His | 7 | 1.2 | 10.1 | — | 11.3 |
| | 9 | 4.3 | 6.7 | — | 11.0 |
| Leu NH$_2$ + AcTyrOEt | 8 | 3.8 | — | 4.9 | 8.7 |
| | 9 | 3.3 | — | 6.5 | 9.8 |
| PhCO.Gly.His + AClyrOEt | 6 | — | 7.2 | 0.8 | 8.0 |
| | 7 | — | 10.1 | 1.1 | 11.2 |
| | 8 | — | 8.9 | 2.4 | 11.3 |
| | 9 | — | 3.6 | 7.6 | 11.2 |
| Leu NH$_2$ + PhCO.Gly.His + AcTYrOET | 7 | 1.2 | 9.6 | 1.0 | 11.8 |
| | 9 | 2.1 | 3.6 | 6.2 | 11.9 |

TABLE VIa
BINDING OF ENZYMES TO NYLON FABRIC SHEETS[a]

| Enzyme | Type of Support | Total Bound Protein (mg/gm) | Active Bound Protein | |
|---|---|---|---|---|
| | | | mg/gm | % of Total |
| A. ACYLHYDRAZIDE DERIVATIVES | | | | |
| Trypsin | Nylon | 0.29 | 0.10 | 35 |
| | PAA-nylon | 0.72 1.56 | 46 | |
| Chymotrypsin | Nylon | 0.24 | 0.09 | 37 |
| | PAA-nylon | 1.10 | 0.54 | 49 |
| Subtilisim BPN' | Nylon | 0.16 | 0.04 | 26 |
| | PAA-nylon | 0.48 | 0.25 | 53 |
| Papain | Nylon | 0.35 | 0.15 | 43 |
| | PAA-nylon | 2.64 | 2.16 | 82 |
| B. AMINOARYL DERIVATIVES | | | | |
| Trypsin | Nylon | 0.33 | 0.14 | 30 |
| | PAA-nylon | 0.50 | 0.38 | 77 |
| Papain | Nylon | 0.52 | 0.21 | 40 |
| | PAA-nylon | 2.16 | 1.53 | 71 |
| Urease | Nylon | 1.00 | 0.82 | 82 |
| | PAA-nylon | 8.16 | 7.33 | 90 |

[a] Coupling of enzyme was carried out by circulating 40 ml of a cold enzyme solution (5 mg/ml) through a column loaded iwth nylon- or polyacrylamide-nylon fabric discs; PAA-nylon, polyacrylamide-nylon graft.

TABLE VIb
ENRICHMENT FACTORS FOR TOTAL PROTEIN AND SPECIFIC ACTIVITY OF ENZYMES BOUND TO POLYACRYLAMIDE-NYLON FABRIC SHEETS[a]

| Enzyme | Coupling Method | Total Protein (A) | Specific Activity (B) | Total Activity[b] (C) |
|---|---|---|---|---|
| Trypsin | acylazide | 5.44 | 1.31 | 7.12 |
| | diazo | 1.29 | 2.13 | 2.75 |
| Papain | acylazide | 7.54 | 1.92 | 14.5 |
| | diazo | 4.12 | 1.77 | 7.31 |
| Chymotrypsin | acylazide | 4.59 | 1.33 | 0.12 |
| | diazo | — | — | — |
| Subtilisin BPN' | acylazide | 2.96 | 2.00 | 5.80 |
| | diazo | — | — | — |
| Urease | acylazide | — | — | — |
| | diazo | 8.16 | 1.10 | 8.96 |

[a] Enrichment factors calculated from data of Table VIa (value for polyacrylamide-nylon enzyme conjugate)/(value for ungrafted nylon-enzyme conjugate).
[b] Calculated from C = A.B.

We claim:

1. A process for coupling at least one nucleophilic group to a polymeric backbone, comprising:
    converting an isocyanide-substituted polymer, the backbone of which is selected from the group consisting of polyamides, polyesters and urea-formaldehyde polymers, to a dihaloisocyanido polymer of the general formula

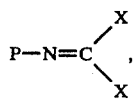

wherein P is the polymeric backbone and X is chlorine or bromine, by reacting the isocyanide-polymer with a solution of the halogen in an inert non-aqueous solvent; and reacting said dihaloisocyanido polymer with a bifunctional or multifunctional nucleophile, wherein said nucleophile is a hydrazide of a dicarboxylic acid.

2. A process for coupling at least one nucleophilic group to a polymeric backbone, comprising:

converting an isocyanide-substituted polymer, the backbone of which is selected from the group consisting of polyamides, polyesters and urea-formaldehyde polymers, to a dihaloisocyanido polymer of the general formula

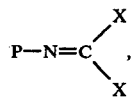

wherein P is the polymeric backbone and X is chlorine or bromine, by reacting the isocyanide-polymer with a solution of the halogen in an inert non-aqueous solvent; and reacting said dihaloisocyanido polymer with a bifunctional or multifunctional nucleophile, wherein said nucleophile is a polymer containing nucleophilic groups capable of reacting with the —NCX$_2$ groups of the dihaloisocyanido polymer.

3. A process for coupling at least one nucleophilic group to a polymeric backbone, comprising:

converting an isocyanide-substituted polymer, the backbone of which is selected from the group consisting of polyamides, polyesters and urea-formaldehyde polymers, to a dihaloisocyanido polymer of the general formula

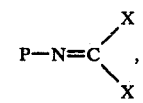

wherein P is the polymeric backbone and X is chlorine or bromine, by reacting the isocyanide-polymer with a solution of the halogen in an inert non-aqueous solvent; and reacting said dihaloisocyanido polymer with a bifunctional or multifunctional nucleophile, wherein said nucleophile is a polyacrylamide partially substituted with acyl hydrazide groups.

4. A process for coupling a biologically active protein to a polymeric backbone, comprising:

converting an isocyanide-substituted polymer, the backbone of which is selected from the group consisting of polyamides, polyesters and urea-formaldehyde polymers, to a dihaloisocyanido polymer of the general formula

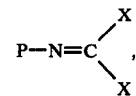

wherein P is the polymeric backbone and X is chlorine or bromine, by reacting the isocyanide-polymer with a solution of the halogen in an inert non-aqueous solvent;

grafting to the dihaloisocyanido polymer a hydrophilic polymer partially substituted with groups capable of reacting with the dihaloisocyanido function; and subsequently reacting the obtained grafted polymer with a biologically active protein.

* * * * *